United States Patent [19]

Verbrugge et al.

[11] 4,056,509

[45] Nov. 1, 1977

[54] PREPARATION OF BENZYL CYANIDES

[75] Inventors: Pieter A. Verbrugge; Elisabeth W. Uurbanus, both of Amsterdam, Netherlands

[73] Assignee: Shell Oil Company, Houston, Tex.

[21] Appl. No.: 699,815

[22] Filed: June 24, 1976

[30] Foreign Application Priority Data

July 9, 1975 United Kingdom ............... 28869/75
July 9, 1975 United Kingdom ............... 28900/75

[51] Int. Cl.$^2$ .................. C07C 120/04; C07C 121/66
[52] U.S. Cl. ............................ 260/465 G; 260/465 R
[58] Field of Search ....................... 260/465 R, 465 G

[56] References Cited

U.S. PATENT DOCUMENTS

| 2,779,781 | 1/1957 | Copelin et al. | 260/465.8 |
| 3,413,309 | 11/1968 | Makosza et al. | 260/465 X |
| 4,012,428 | 3/1977 | Ohno et al. | 260/465 G |

FOREIGN PATENT DOCUMENTS 1,227,144  4/1971  United Kingdom.

OTHER PUBLICATIONS

Starks, J. Amer. Chem. Soc., vol. 93, pp. 195–199 (1971).

*Primary Examiner* — Dolph H. Torrence

[57] ABSTRACT

Optionally ring-substituted benzyl cyanides are prepared by reacting the corresponding benzyl halide with an aqueous phase containing cyanide ions in the presence of a liquid organic phase containing (a) the benzyl halide, (b) a salt which dissociates in water to form cyanide ions, and (c) an onium salt or hydroxide, which reaction is conducted in the absence of water or using an amount of water to benzyl halide below about 0.1. The resulting cyanides can be alkylated at the alpha position using a sec-alkyl halide.

15 Claims, No Drawings

PREPARATION OF BENZYL CYANIDES

BACKGROUND OF THE INVENTION

1. Field of the Invention

The present invention relates to a new process for the preparation of benzyl cyanides optionally substituted in the aromatic ring and to alkylation of such cyanides at the alpha position.

2. Description of the Prior Art

A process of catalyzing heterogeneous ionic reactions in which the reactants are located in different liquid phases of different polarity is described in British Pat. No. 1,227,144. In this patent, the volume ratio calculated from the volume of the water excluding any dissolved material and from the starting volume of organic reactant (such as alkyl halide,) is disclosed in the examples as being in the range of from 0.2 to 1.4. Fairly high volume ratios are also mentioned in other examples of processes for conducting heterogeneous reactions described in the literature. For example, the volume ratios disclosed in Journal of the American Chemical Society 93 (1971), pages 195–199 and in Chemical Pharmaceutical Bulletin 10, (1962), pages 427–429 are 0.2 and 3.9, respectively.

Chemical Abstracts 64 (1966) 17475–17476 describes the catalytic alkylation of benzyl cyanide at the alpha position by mixing an organic phase containing benzyl cyanide and an alkyl chloride or bromide with a 50% w aqueous sodium hydroxide solution in the presence of benzyltriethylammonium chloride. Thus, a mixture of 25 mmol of benzyl cyanide, 9 ml of a 50% w aqueous sodium hydroxide solution. 0.25 mmol of benzyltriethylammonium chloride and 40 mmol of an alkyl chloride or bromide was shaken for 1 hour. The chlorides were far less reactive with respect to alkylation than the corresponding bromides, the conversions of the halide when isopropyl chloride and isopropyl bromide were used, being 2% and 43%, respectively. This, of course, implies that the conversion of the benzyl cyanide and the yield of 3-methyl-2-phenyl-butanenitrile had been correspondingly low. The very low conversion of 2% strongly suggests that isopropyl chloride is unsuitable for the commercial isopropylation of benzyl cyanide.

SUMMARY OF THE INVENTION

It has now been found that certain normally heterogeneous reactions can be conducted advantageously when extremely low volume ratios of water to organic reactant are applied and that such a process can even be modified by using no water at all.

The present invention can then be defined as relating to a process for the preparation of optionally ring-substituted benzyl cyanides by means of a reaction represented by the equation

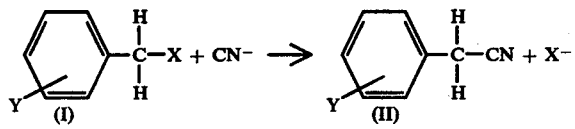

wherein Y is hydrogen or a halogen atom of atomic number 9–35, inclusive, and X is a halogen atom of atomic number 17–53, inclusive, and performed in the presence of a liquid organic phase containing (a) the optionally ring-substituted benzyl halide, (b) a salt which dissociates in water with the formation of cyanide anions $CN^-$, and (c) a tetrahydrocarbylonium salt or hydroxide of an element of Group VA of the Periodic Table of the Elements, which process is conducted either in the absence of water or using a volume ratio of water to optionally ring-substituted benzyl halide below about 0.1.

The optionally ring-substituted benzyl halides of formula I are usually converted to a very large extent and with a very high selectivity to the corresponding benzyl cyanides of formula II. The selectivity to a compound is defined as the yield of this compound calculated on the amount of the optionally ring-substituted benzyl halide of formula I that has reacted. The conversion and selectivity to the corresponding benzyl cyanide of formula II are often both 100%. The extremely low volume ratio of water to the optionally ring-substituted benzyl halide of formula I offers the advantages of a low water consumption and of the possibility to use a reactor of small dimensions.

The period of time required to reach the moment of maximum conversion of the optionally ring-substituted benzyl halide of formula I is acceptable even when no water is applied. The presence of water reduces this period. The volume ratio is preferably in the range of from 0.0001 to 0.04 and particularly preferred is the range of from 0.001 to 0.02. When the process of the present invention is modified by deleting the tetrahydrocarbylonium salt or hydroxide either no reaction or hardly any reaction can be detected.

The prior art processes described above are conducted with an excess of anion, such as cyanide anion, in order to offset the partition effect of the displaced halide anion. However, the process of the present invention allows use of about equal molar amounts of cyanide anion $CN^-$ and the optionally ring-substituted benzyl halide of formula I; even under such reaction condition the above-mentioned high conversions and selectivities are still obtained. Preferably, the molar ratio of cyanide anion $CN^-$ to optionally ring-substituted benzyl halide of formula I is in the range of 1 to 1.1.

As has been mentioned above, the atom or group X in the equation represents a halogen atom of atomic number 17–53, inclusive. The preferred halogen atom is a chlorine or bromine atom. In the equation Y represents a hydrogen atom or a halogen atom of atomic number 9–35, inclusive. Preferably Y is a chlorine or bromine atom. p-Chlorobenzyl chloride has been found to be a particularly good starting material of formula I.

The process is suitably carried out with vigorous stirring at temperatures of from 25° to 100° C, particularly of from 70° to 90° C.

The tetrahydrocarbylonium salt can be a tetrahydrocarbylammonium, -phosphonium, -arsonium or -stibonium salt or an onium salt derived from bismuth. A mixture of such salts can be used. The cation of the tetrahydrocarbylonium salt can contain one or more quaternary bound atoms of Group VA. The hydrocarbyl groups can be alkyl, cycloalkyl, alkenyl or aryl groups or a combination of any of these groups, for example, alkaryl groups. The anion of the tetrahydrocarbylonium salt can be for instance, equal to the anion $CN^-$; it can be, for example a halide or a hydroxyl ion; chlorides and bromides are preferred. Nitrogen and phosphorus are preferred among the elements of Group VA, nitrogen being most preferred. The total number of carbon atoms in the four hydrocarbyl groups can be from 12 to 70 when an aqueous phase is present and preferably 16 to 34. Examples of preferred tetrahydrocarbylonium salts are tetraalkylammonium halides such as tetra-n-butylammonium chloride, tetra-n-pentylammonium chloride, ethyl-tri-sec-octylammonium chloride, ethyl-tri-n-hexylammonium chloride, n-hexadecyltri-n-hexyl-ammonium chloride, di-n-undecyldiethylammonium chloride, tetra-n-octyl-ammonium chloride, or aryltrialkylammonium compounds such as benzyltri-n-butylammonium chloride. The corresponding phosphonium compounds and bromides of both the ammonium and phosphonium compounds are also useful.

The molar ratio of the tetrahydrocarbylonium salt to optionally ring-substituted benzyl halide of formula I can vary within a wide range. In general, this molar ratio is below 0.2 and usually molar ratios between 0.0001 and 0.1 are sufficient to achieve a satisfactory rate of reaction.

The reaction mixture obtained in the process of the present invention contains a salt which dissociates in water with formation of anions $CN^-$, usually present partly in the solid state, with either a very small amount of an aqueous phase saturated with this salt or no water at all. The water present in the aqueous phase can be bound by the addition of a drying agent, for example, anhydrous calcium chloride. Then, the solid material can be filtered off from the dried mixture and the organic phase obtained as a filtrate can be distilled to isolate the resulting benzyl cyanide of formula II. The solid material filtered off can be washed with a solvent, for example, diethyl ether or chloroform and the washings obtained can be added to the filtrate before the distillation.

The novel process is particularly suitable for the preparation of the optionally ring-substituted benzyl cyanides of formula II in the presence of a tetrahydrocarbylammonium salt or hydroxide, because such compounds are readily alkylated in a liquid organic phase also containing a sec-alkyl halide.

When the process of the present invention is conducted with such a small amount of water, if any, no intermediate removal of the aqueous phase is necessary prior to addition of the sec-alkyl halide and the aqueous alkali metal hydroxide solution required for the subsequent alkylation of the benzyl cyanides of formula II.

The present invention is thus also directed to a process for the preparation of compounds of the formula

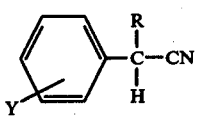
(III)

wherein R represents a secondary alkyl group; and Y represents a hydrogen atom or a halogen atom of atomic number from 9–35, inclusive, which process comprises contacting an organic phase containing a compound of the formula

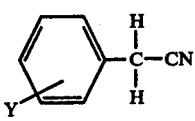
(II)

and a sec-alkyl halide of the formula $$Hal - R \qquad (IV)$$

in which formulas II and IV R and Y have the meanings stated above and Hal represents a halogen atom having an atomic number from 17 to 53, inclusive, with an aqueous phase containing an alkali metal hydroxide or with a solid alkali metal hydroxide in the presence of a quaternary ammonium salt or hydroxide, using a molar ratio of sec-alkyl halide of formula IV to a compound of formula II of at least 3.

When the process according to the invention is modified by applying a molar ratio of sec-alkyl halide to the compound of the formula II below 3 in the presence of a solvent, for example diethyl ether or dioxane, the compounds of the formula II will react at an unacceptably low rate, if at all. However, when, according to the invention, this molar ratio is increased above 3, the conversion of the compounds of the formula II becomes progressively higher at a surprisingly high rate. This is a very attractive feature of the invention. The abovementioned molar ratio is preferably in the range of from 5 to 20. Molar ratios above 20 may be used but usually do not offer additional advantages.

The excellent results of the two embodiments described hereinafter are fully unexpected in view of the prior art mentioned hereinbefore.

According to one embodiment of the present invention the organic phase containing a compound of the formula II and sec-alkyl halide is contacted with an aqueous phase containing an alkali metal hydroxide. This often results in full conversion of the compound of the formula II after a short reaction time, for example, 0.25 to 2 hours and in a selectivity to compounds of the formula III of usually 100% or almost 100% with dialkyllated compounds hardly being formed, if at all. The selectivity to a compound is the yield of this compound calculated on the amount of the starting compound of the formula II that has reacted.

A suitable alkali metal hydroxide is, for example, sodium hydroxide, or potassium hydroxide, which is preferably present in the aqueous phase in a concentration of at least 40, preferably 50% by weight. Sodium hydroxide is preferred.

Very good results have been obtained with benzyl cyanide. The reaction times are usually particularly short, for example, 0.5 hour, when phenyl groups substituted with halogen atoms at the position para with respect to the —CH$_2$CN group shown in the formula II, is applied. P-Chlorobenzyl cyanide is a very suitable compound of the formula II.

The sec-alkyl halide of the formula IV may be a chloride, bromide or iodide. Chlorides are preferred. Examples of sec-alkyl chlorides are isopropyl chloride, 2-chlorobutane, 2-chloropentane, 3-chloropentane, 2-chloro-3-methylbutane and 2-chloro-4-methyl-pentane and the corresponding bromides and iodides. Very good results have been obtained with isopropyl chloride.

The quaternary ammonium salt or hydroxide has four hydrocarbyl groups — which optionally may be substituted — attached to the nitrogen atom, for example, aromatic, aliphatic, cycloaliphatic or unsaturated groups or combinations of any of these groups, for example as aromatic-aliphatic group. The cation of the tetrahydrocarbylammonium salt or hydroxide may contain one or more quaternary bound nitrogen atoms. The salt may have any anion; chlorides and bromides are preferred. The total number of carbon atoms in the four hydrocarbyl groups is preferably from 12 to 70. Examples of suitable tetrahydrocarbylammonium salts are tetraalkylammonium halides such as tetra-n-butylammonium chloride, tetra-n-pentylammonium chloride, ethyl-tri-sec-octylammonium chloride, ethyl-tri-n-hexylammonium chloride, n-hexadecyltri-n-hexylammonium chloride, di-n-undecyldiethylammonium chloride and tetra-n-octylammonium chloride, or aryltrialkylammonium halides such as benxyltri-n-butylammonium chloride and the corresponding bromides. The quaternary ammonium salt and/or hydroxide is/are preferably applied in (an) amount(s) of less than 0.2 mol and in particular between 0.01 and 0.0001 mol per mol of the compound of the formula II.

The process is suitably carried out by vigorous stirring of the aqueous phase (or the solid alkali metal hydroxide) and organic phase, at temperatures of from 25° C to 60° C, preferably 35° C to 40° C.

The compounds of the formula III may be isolated from the reaction mixture by filtration of the suspended alkali metal compounds, separating the filtrate into aqueous phase and an organic phase (if required) and washing (with water), drying and boiling down the organic phase. The sec-alkyl halide of the formula IV thus recovered may be reused.

Preparation of the compounds of the formula II in accordance with the invention allows subsequent addition to the reaction mixture of merely the aqueous solution containing an alkali metal hydroxide and/or the solid alkali metal hydroxide and the sec-alkyl halide of the formula IV, thus obviating any isolation of compounds and intermediate removal of an aqueous phase. The said volume ratio is preferably in the range of from 0.0001 to 0.04 and particularly of from 0.001 to 0.02. The group X preferably represents a chlorine or bromine atom.

Optionally substituted benzyl cyanides of formula II are valuable intermediates and can be alkylated to compounds of formula IV and then hydrolyzed to form acids which are especially useful in the preparation of pesticides containing, for example, a 2-(4-chlorophenyl)-3-methylbutanoyloxy group. The 2-(4-chlorophenyl)-3-methylbutanoyloxy compounds are suitably used in the preparation of esters of alpha-cyano-m-aryloxybenzyl alcohol, which possess interesting pesticidal, in particular insecticidal properties and which are described in Belgian patent publication No. 801,946.

The process is further illustrated by means of the following examples, which examples are for the purpose of illustration and which should not be regarded as limiting the invention in any way.

EXAMPLE I p-Chlorobenzyl chloride (30 mmol=4.36 ml), sodium cyanide (30 mmol), tetra-n-butylammonium chloride (0.036 mmol) and water (0.05 ml) were mixed in a vessel fitted with a paddle stirrer, a thermometer and a water-cooled reflux condenser and the contents of the vessel were stirred at a temperature of 70° C for a period of 3 hours, the volume ratio between the water and the p-chlorobenzyl chloride being 0.011. At the end of this period the conversion of the p-chlorobenzyl chloride was 95%. Then, the temperature of the reaction mixture was increased to 85° C. After 30 minutes stirring at this temperature the p-chlorobenzyl chloride was fully converted, with a selectivity to p-chlorobenzyl cyanide of 100%. Subsequently, the mixture was cooled to a temperature of 40° C and 220 mmol of isopropyl chloride and 30 ml of 50% w aqueous sodium hydroxide solution were added, the molar ratio of isopropyl chloride to p-chlorobenzyl cyanide being 7.3. After stirring for one hour the p-chlorobenzyl cyanide was fully converted with a selectivity to 2-(4-chlorophenyl)-3-methylbutanenitrile of 100%.

EXAMPLE II p-Chlorotoluene (62 mmol), sulphuryl chloride (5 ml) and benzoyl peroxide (0.04 mmol) were mixed in the vessel used in Example I and the contents of the vessel were stirred at a temperature of 85° C. After 2 hours stirring the conversion of p-chlorotoluene was 90% with a selectivity to p-chlorobenzyl chloride of 100%. Then, 5.5 mmol (=0.1 ml) of water was introduced and subsequently solid sodium bicarbonate was added until the pH has reached a value of 7. Then 60 mmol of solid sodium cyanide and 1.8 mmol of tetra-n-butylammonium chloride were added to the neutralized mixture. The contents of the vessel — in which the volume ratio of water to p-chlorobenzyl cyanide was 0.012 — were stirred for a period of 3 hours at a temperature of 85° C. At the end of this period the p-chlorobenzyl chloride was fully converted with a selectivity to p-chlorobenzyl cyanide of 100%. Then, the reaction mixture was cooled to a temperature of 40° C and 660 mmol of isopropyl chloride was added, the molar ratio of isopropyl chloride to p-chlorobenzyl cyanide being 11.8. Subsequently 60 ml of a 50% w aqueous sodium hydroxide solution was added dropwise. After 3 hours stirring the p-chlorobenzyl cyanide was fully converted with a selectivity to 2-(4-chlorophenyl)-3-methylbutanenitrile of 100%.

EXAMPLE III p-Chlorobenzyl chloride (30 mmol=4.36 ml), sodium cyanide (30 mmol), tetra-n-butylammonium chloride (0.036 mmol) and water (0.05 ml) were mixed in the vessel used in Example I and the contents of the vessel were stirred at a temperature of 75° C, the volume ratio between the water and the p-chlorobenzyl chloride being 0.011. After 3 hours stirring the p-chlorobenzyl chloride was fully converted with a selectivity to p-chlorobenzyl cyanides of 100%.

EXAMPLE IV p-Chlorobenzyl chloride (30 mmol=4.36 ml), sodium cyanide (30 mmol) and tetra-n-butylammonium chloride (0.036 mmol) were mixed in the vessed used in Example I and the contents of the vessel were stirred at a temperature between 60° C and 70° C. After 8 hours' stirring the conversion of the p-chlorobenzyl chloride was 90% with a selectivity to p-chlorobenzyl cyanide of 100%.

EXAMPLE V

The experiments 1–16 listed in the table were carried out in a vessel fitted with a paddle stirrer, a thermometer and a water-cooled reflux condenser. Isopropyl chloride was used as the alkylating agent. The table states the compounds to be alkylated (column 2), the solvent, if any (column 5), the alkali metal hydroxide (column 7), the tetrahydrocarbylammonium salt (column 8), the amounts in which the latter four materials were used, the molar ratio of isopropyl chloride to the compound to be alkylated (column 4), the temperature of the contents of the vessel (column 10) and the time allowed for reaction in the vessel (column 11). The table also gives the conversion of the compound to be alkylated (column 12) and in column 14 the selectivity to the compounds stated in column 13, as measured by GLC analysis of a sample of the reaction mixture.

The experiments were conducted as follows:

Experiment 1: The tetrahydrocarbylammonium salt and the alkali metal hydroxide solution were added to a solution of the compound to be alkylated in the solvent. Isopropyl chloride was added dropwise to the mixture thus obtained and evaporated as soon as it came into contact with the liquid.

Experiments 2, 3, 8, 11, 12, 13, 14 and 15: The tetrahydrocarbylammonium salt and the alkali metal hydroxide solution were added to a mixture of the compound to be alkylated and the isopropyl chloride.

Experiments 4, 7 and 16: The tetrahydrocarbylammonium salt was added to a mixture of the compound to be alkylated and isopropyl chloride. The temperature was raised to between 35° and 40° C and subsequently the alkali metal hydroxide solution was added.

Experiment 5: This experiment was conducted in the same manner as experiment 2, but 8.5 mmol of powered potassium hydroxide was used instead of 20 ml of 50% w aqueous sodium hydroxide.

Experiment 6: This experiment was conducted in the same manner as experiment 2, but 142 mmol of powdered potassium hydroxide was used instead of 20 ml of 50 %w aqueous sodium hydroxide.

Experiment 9: The tetrahydrocarbylammonium salt and the aqueous sodium hydroxide solution were added to a solution of the compound to be alkylated and the isopropyl chloride in diethyl ether.

TABLE

| Exp. No. | Compound to be alkylated name | amount mmol | molar ratio of isopropylchloride to compound to be alkylated | solvent name | amount ml | 50 %w aqueous NaOH, ml | tetrahydrocarbyl-ammonium salt name | amount mmol | reaction temp. °C | reaction time h | conversion, % | selectivity to compound | selectivity to % |
|---|---|---|---|---|---|---|---|---|---|---|---|---|---|
| 1* | benzyl cyanide | 17 | not relevant | 1,2-dimethoxyethane | 10 | 20 | tetra-n-butylammonium chloride | 0.036 | 60 | not relevant | 0 | | |
| 2* | " | 17 | 1.5 | none | | 20 | " | 0.036 | 40 | 8 | 0 | 3-methyl-2-phenyl-butanenitrile | 100 |
| 3 | " | 8.5 | 12.9 | none | | 20 | " | 0.036 | 35 | 2 | 100 | " | |
| 4 | " | 8.5 | 12.9 | none | | 20 | " | 0.036 | 35–40 | 2 | 100 | " | 100 |
| 5 | " | 8.5 | 12.9 | none | | 8.5 mmol powdered KOH | " | 0.036 | 35–40 | 24 | 90 | 3-cyano-2,4-dimethyl-3-phenylpentane | 90 10 |
| 6 | " | 8.5 | 12.9 | none | | 142 mmol powdered KOH | methyl-tri-sec-octyl-ammonium chloride | 0.036 | 35–40 | 3 | 100 | 3-methyl-2-phenyl-butanenitrile | 100 |
| 7 | " | 8.5 | 12.9 | none | | 20 | " | 0.062 | 35–40 | 2 | 100 | " | 100 |
| 8* | 4-chlorobenzyl cyanide | 132 | 1.1 | none | | 100 | tetra-n-butylammonium chloride | 1.4 | 36.5 | 24 | 5 | 2-(4-chlorophenyl)-3-methylbutanenitrile | 100 |
| 9* | " | 6.6 | 2.1 | diethyl ether | 10 | 20 | " | 0.036 | 36.5 | 7 | 68 | " | 100 |
| 10 | " | 6.6 | 16.7 | none | | 20 | " | 0.036 | 36.5 | 0.5 | 100 | " | 100 |
| 11 | " | 29.7 | 16.7 | none | | 90 | " | 0.072 | 40 | 2 | 100 | " | 100 |
| 12 | " | 29.7 | 16.7 | none | | 45 | " | 1.44 | 40 | 3 | 100 | " | 100 |
| 13 | " | 29.7 | 16.7 | none | | 45 | " | 1.80 | 40 | 2 | 100 | " | 93.5 |
| 14 | " | 29.7 | 22.2 | none | | 45 | " | 1.44 | 40 | 2 | 93 | 2-(4-chlorophenyl)-3-methylbutanenitrile 3-(4-chlorophenyl)-3-cyano-2,4-dimethylpentane | 65 |
| 15* | " | 6.6 | 16.7 | none | | 20 | tetraethylphosphonium iodide | 0.036 | 40 | 3 | 100 | 2-(4-chlorophenyl)-3-methylbutanenitrile | 100 |
| 16 | tert-butyl phenylacetate | 8.5 | 12.9 | none | | 20 | tetra-n-butylammonium chloride | 1.1 | 35–40 | 6 | 100 | tert-butyl 3-methyl-2-phenylbutanoate | 100 |
| col. No. 1 | 2 | 3 | 4 | 5 | 6 | 7 | 8 | 9 | 10 | 11 | 12 | 13 | 14 |

*not according to the invention

The following additional results were obtained:

Experiment 5: After 24 hours' stirring 1.4 mmol of powdered potassium hydroxide was added to the reaction mixture and stirring continued for an additional period of 24 hours. The conversion was 100% at the end of the latter period, the selectivities to 3-methyl-2-phenylbutanenitrile and to 3-cyano-2,4-dimethyl-3-phenylpentane being 85% and 15%, respectively.

Experiment 8: After 24 hours' stirring 0.12 mmol of methyl-tri-sec-octylammonium chloride was added and stirring was continued for 48 hours. The conversion at the end of the latter period was 75%, with a selectivity to 2-(4-chlorophenyl)-3-methylbutanenitrile of 100%.

Experiment 10: At reaction times beyond 30 minutes 3-cyano-2,4-dimethyl-3-phenylpentane was found.

Experiment 12: The sodium chloride was filtered off from the reaction mixture and the filtrate was allowed to separate into an aqueous phase and an organic phase, which was washed with an equal volume of water, dried over anhydrous magnesium sulphate and boiled down to obtain a residue consisting of 2-(4-chlorophenyl)-3-methylbutanenitrile. The weight of this residue corresponded to a yield of 89% calculated on starting 4-chlorobenzyl cyanide.

Experiment 14: 2-(4-chlorophenyl)-3-methylbutanenitrile was isolated in the same manner as in experiment 12, in a yield of 93%.

EXAMPLE VI p-Chlorobenzyl chloride (30 mmol = 4.36 ml), sodium cyanide (30 mmol), tetra-n-butylammonium chloride (0.036 mmol) and water (0.05 ml) were mixed in a vessel fitted with a paddle stirrer, a thermometer and a water-cooled reflux condenser and the contents of the vessel were stirred at a temperature of 70° C for a period of 3 hours, the volume ratio between the water and the 4-chlorobenzyl chloride being 0.011. At the end of this period the conversion of the p-chlorobenzyl chloride was 95%. Then, the temperature of the reaction mixture was increased to 85° C. After 30 minutes stirring at this temperature the p-chlorobenzyl was fully converted, with a selectivity to p-chlorobenzyl cyanide of 100%. Subsequently, the mixture was cooled to a temperature of 40° C and 220 mmol of isopropyl chloride and 30 ml of 50% w aqueous sodium hydroxide solution were added, the molar ratio of isopropyl chloride to p-chlorobenzyl cyanide being 7.3. After stirring for 1 hour the p-chlorobenzyl cyanide was fully converted with a selectivity to 2-(4-chlorophenyl)-3-methylbutanenitrile of 100%.

We claim:

1. A process for the preparation of compounds of the formula

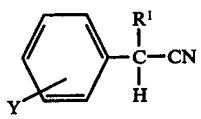

(III)

wherein $R^1$ represents a secondary alkyl group having from 3 to 6 carbon atoms; and Y represents a hydrogen atom or a halogen atom of atomic number from 9–35, inclusive, which process comprises contacting an organic phase containing a compound of the formula

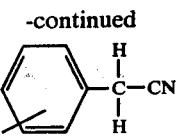

(II)

and a sec-alkyl halide of the formula $$Hal - R^1$$ (IV)

in which formulas II and IV $R^1$ and Y have the meanings stated above and Hal represents a halogen atom having an atomic number from 17 to 53, inclusive, with an aqueous phase containing an alkali metal hydroxide or with a solid alkali metal hydroxide in the presence of a tetrahydrocarbylammonium halide, using a molar ratio of sec-alkyl halide of formula IV to compound of formula II of at least 3.

2. A process as claimed in claim 1, in which the molar ratio of sec-alkyl halide to the compound of the formula II is in the range of from 5 to 20.

3. A process as claimed in claim 1, in which the organic phase contains a compound of the formulas II and is contacted with an aqueous phase containing an alkali metal hydroxide.

4. A process as claimed in claim 1, in which the alkali metal hydroxide is sodium hydroxide.

5. A process as claimed in claim 4, in which the sodium hydroxide is present in the aqueous phase in a concentration of at least 40% by weight.

6. A process as claimed in claim 1, in which the organic phase contains a compound of the formula II and is contacted with a solid alkali metal hydroxide using a molar ratio of alkali metal hydroxide to the compound of the formula II of at least 2.

7. A process as claimed in claim 6, which is conducted with benzyl cyanide as the compound of the formula II.

8. A process as claimed in claim 6, which is conducted with p-chlorobenzyl cyanide as the compound of the formula II.

9. A process as claimed in claim 1, which is conducted with a sec-alkyl chloride as the compound of the formula IV.

10. A process as claimed in claim 9, which is conducted with isopropyl chloride as the compound of the formula IV.

11. A process as claimed in claim 1, in which the tetrahydrocarbylammonium halide is used in an amount in the range of from 0.0001 to 0.2 mol per mol of the compound of the general formula II.

12. A process as claimed in claim 1, which is conducted at a temperature in the range of from 25° C to 60° C.

13. A process as claimed in claim 1 wherein the tetrahydrocarbylammonium halide is a tetraalkylammonium halide in which the total number of carbon atoms in the four alkyl groups is 16 to 34.

14. A process for the preparation of substituted benzyl nitrile derviatives which comprises (a) reacting a benzyl halide of the formula

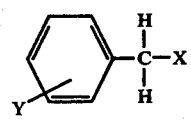

(I)

wherein Y represents a hydrogen atom or a halogen atom of atomic number from 9 to 35, inclusive, and X represents a halogen atom of atomic number 17 to 53, inclusive, with sodium cyanide, which reaction is performed in the presence of a liquid organic phase containing the benzyl halide, sodium cyanide and a tetrahydrocarbylammonium halide, either in the absence of water or using a volume ratio of water to benzyl halide of below 0.1 and (b) reacting the resulting organic phase containing a benzyl nitrile with a sec-alkyl halide of the formula Hal—R$^1$ wherein R$^1$ represents a secondary alkyl group having from 3 to 6 carbon atoms and Hal represents a halogen atom having an atomic number of from 17 to 53, inclusive, with an aqueous phase containing an alkali metal hydroxide or with a solid alkali metal hydroxide also in the presence of the tetrahydrocarbylammonium halide and using a molar ratio of sec-alkyl halide reactant to benzyl nitrile reactant of at least 3.

15. A process as claimed in claim 14, in which the volume ratio of water to the compound of the formula I is in the range of from 0.0001 to 0.04.

* * * * *